US011395709B2

(12) United States Patent
Matsuda et al.

(10) Patent No.: US 11,395,709 B2
(45) Date of Patent: Jul. 26, 2022

(54) CONTROL SYSTEM, CONTROL METHOD, AND SURGICAL ARM SYSTEM

(71) Applicant: Sony Corporation, Tokyo (JP)

(72) Inventors: Yasuhiro Matsuda, Tokyo (JP); Jun Arai, Kanagawa (JP); Takara Kasai, Kanagawa (JP); Yohei Kuroda, Tokyo (JP); Wataru Kokubo, Tokyo (JP)

(73) Assignee: SONY CORPORATION, Tokyo (JP)

( * ) Notice: Subject to any disclaimer, the term of this patent is extended or adjusted under 35 U.S.C. 154(b) by 441 days.

(21) Appl. No.: 16/484,467

(22) PCT Filed: Jan. 12, 2018

(86) PCT No.: PCT/JP2018/000665
§ 371 (c)(1),
(2) Date: Aug. 8, 2019

(87) PCT Pub. No.: WO2018/159114
PCT Pub. Date: Sep. 7, 2018

(65) Prior Publication Data
US 2020/0000535 A1    Jan. 2, 2020

(30) Foreign Application Priority Data

Feb. 28, 2017    (JP) .............................. JP2017-035965

(51) Int. Cl.
*G05B 15/00*    (2006.01)
*G05B 19/00*    (2006.01)
(Continued)

(52) U.S. Cl.
CPC ............. *A61B 34/37* (2016.02); *B25J 9/0096* (2013.01); *B25J 9/1633* (2013.01); *A61B 90/50* (2016.02);
(Continued)

(58) Field of Classification Search
CPC ...... A61B 2034/2059; A61B 2090/064; A61B 2090/066; A61B 34/37; A61B 90/361;
(Continued)

(56) References Cited

U.S. PATENT DOCUMENTS

2007/0173788 A1* 7/2007 Schena .................. A61B 34/37
606/1
2017/0079729 A1* 3/2017 Fukushima ............ B25J 9/1633
(Continued)

FOREIGN PATENT DOCUMENTS

JP    2002-187078 A    7/2002
JP    2009-537231 A    10/2009
(Continued)

OTHER PUBLICATIONS

International Search Report and Written Opinion dated Mar. 13, 2018 for PCT/JP2018/000665 filed on Jan. 12, 2018, 9 pages including English Translation of the International Search Report.

*Primary Examiner* — Harry Y Oh
(74) *Attorney, Agent, or Firm* — Xsensus LLP

(57) ABSTRACT

There is provided a control system for controlling a surgical arm device of a multi-link structure in which a plurality of links is coupled together by a joint unit in a force control mode.

In generalized inverse dynamics, the control system sets a motion purpose and a constraint condition in an operation space describing an inertia of force acting on a multi-link structural body and an acceleration of the multi-link structural body, and for implementing an operation space acceleration indicating the motion purpose, calculates a virtual force acting on the operation space on the basis of a motion equation relating to the operation space including a term of an operation space bias acceleration in consideration to gravity compensation according to inclination information (Continued)

of the surgical arm device, and calculates a torque command value for a joint unit on the basis of a real force converted from the virtual force.

14 Claims, 9 Drawing Sheets

(51) Int. Cl.
*A61B 34/37* (2016.01)
*B25J 9/16* (2006.01)
*B25J 9/00* (2006.01)
*A61B 34/20* (2016.01)
*A61B 90/50* (2016.01)
*A61G 13/04* (2006.01)

(52) U.S. Cl.
CPC ...... *A61B 2034/2059* (2016.02); *A61G 13/04* (2013.01)

(58) Field of Classification Search
CPC .......... A61B 90/50; A61G 13/04; B25J 13/00; B25J 9/1607; B25J 9/1633; G05B 2219/42153
See application file for complete search history.

(56) References Cited

U.S. PATENT DOCUMENTS

| 2018/0071049 A1* | 3/2018 | Nowatschin | A61B 90/50 |
| 2018/0289445 A1* | 10/2018 | Krinninger | A61B 34/25 |

FOREIGN PATENT DOCUMENTS

| JP | 2011-212835 A | 10/2011 |
| JP | 2016-518199 A | 6/2016 |
| JP | 2017-019080 A | 1/2017 |
| WO | 2015/046081 A1 | 4/2015 |
| WO | 2016/069648 A1 | 5/2016 |

* cited by examiner

700

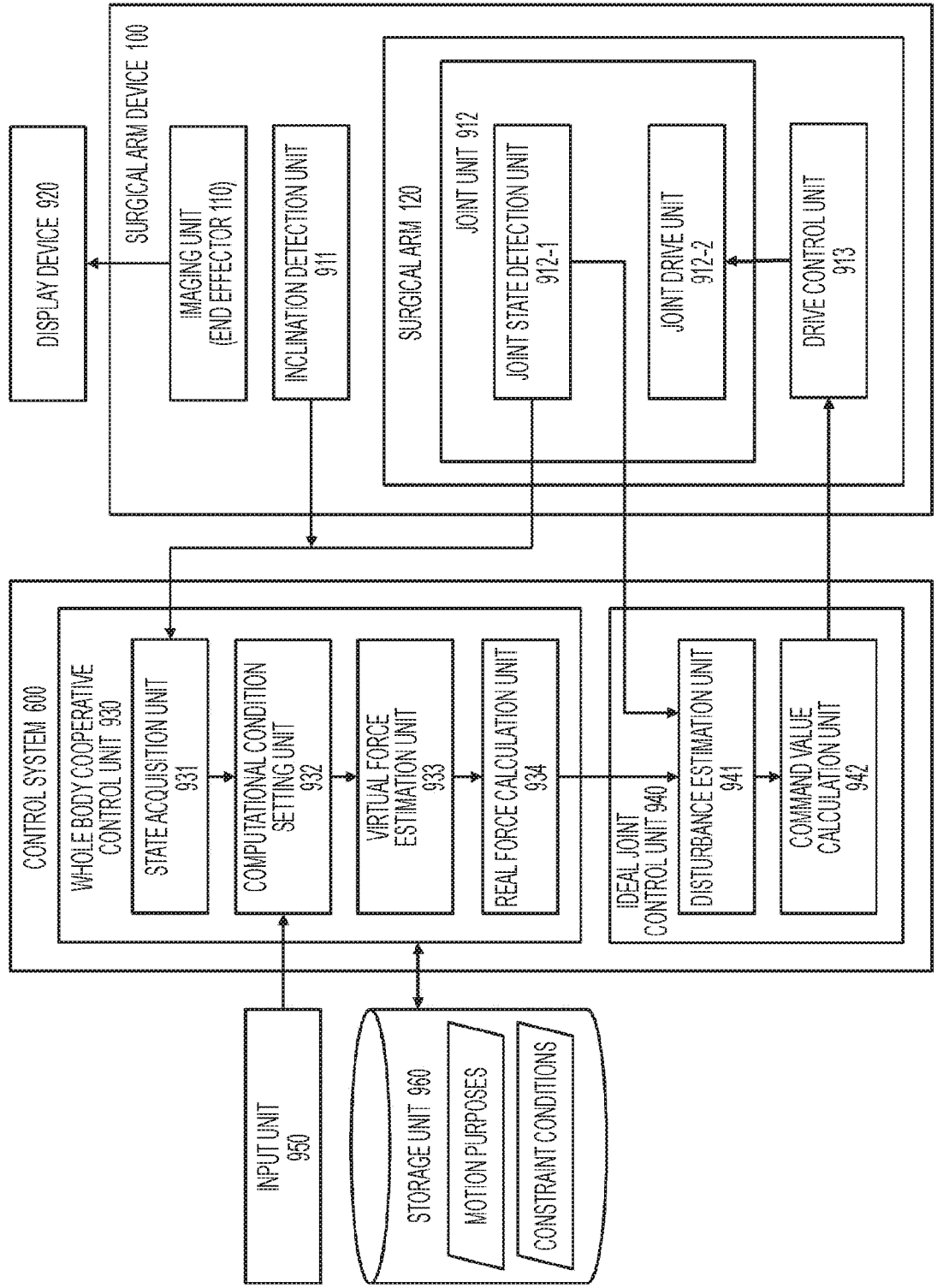

United States Patent US 11,395,709 B2

CONTROL SYSTEM, CONTROL METHOD, AND SURGICAL ARM SYSTEM

CROSS-REFERENCE TO RELATED APPLICATIONS

The present application is based on PCT filing PCT/JP2018/000665, filed Jan. 12, 2018, which claims priority to JP 2017-035965, filed Feb. 28, 2017, the entire contents of each are incorporated herein by reference.

TECHNICAL FIELD

A technique disclosed herein relates to a control system and a control method for controlling an arm device of a multi-link structure in which a plurality of links is coupled together by joint units in a force control mode, and a surgical arm system, for example, relates to a control system and a control method for controlling a surgical arm device applied to a medical field in a force control mode, and a surgical arm system.

BACKGROUND ART

In recent years, there have been popularized surgical arm devices in various industrial fields including a medical field. Replacing at least part of human work by surgical arm devices makes it possible to implement high accuracy and high performance of the work.

The surgical arm device is a multi-link structural body in which a plurality of links is coupled together by joint units, for example. Controlling rotational driving of the plurality of joint units makes it possible to implement desired actions of the entire surgical arm device. Examples of a control method of the surgical arm device and the joint units include position control and force control. In the position control, a position command value of angle and the like is given to an actuator of the joint units, and driving of the joint units is controlled in such a manner as to follow the command value. On the other hand, in the force control, a target value of force to be applied to a work target by the surgical arm device is given, for example, and driving of the joint units (for example, torque generated at the joint units) is controlled to implement the force indicated by the target value.

The position-controlled surgical arm device is easy to make a system configuration but has difficulty in flexible response to external force. In contrast to this, the force-controlled surgical arm device is complicated in system configuration but can flexibly respond to external force, which is suited to perform tasks (motion purposes) through various physical interactions with the external world. In particular, a medical surgical arm device is expected to operate in proximity to a surgical operator and assistants in a narrow operating room and implement interpersonal physical interactions, and thus can be said to preferably perform force control.

For example, there has been proposed a surgical arm device that includes: a plurality of joint units that couples a plurality of links to implement at least six or higher degrees of freedom for driving of a multi-link structural body including the plurality of links; and a drive control unit that performs a force control of driving of the joint units on the basis of a state of the joint units (for example, refer to Patent Document 1). A tip unit including a medical instrument such as an endoscope or forceps is attached to the tip of the multi-link structural body of this kind of surgical arm device.

CITATION LIST

Patent Document

Patent Document 1: WO 2015/046081 A
Patent Document 2: Japanese Translation of PCT International Application Publication No. 2016-518199

SUMMARY OF THE INVENTION

Problems to be Solved by the Invention

An object of a technique disclosed herein is to provide a control system and a control method for controlling a surgical arm device of a multi-link structure in which a plurality of links is coupled together by a joint unit in a force control mode, and a surgical arm system.

Solutions to Problems

A technique disclosed herein is devised in view of the foregoing issue. A first aspect of the technique is a control system that controls a surgical arm device. The control system includes: an inclination information acquisition unit that acquires inclination information of the surgical arm device; a setting unit that sets a computational condition including gravity compensation according to the inclination information; and a computation unit that calculates a command value to the surgical arm device according to the computational condition.

However, the "system" here refers to an object in which a plurality of devices (or functional modules implementing specific functions) is logically assembled, and the devices or functional modules may be or may not be accommodated in a single housing.

The surgical arm device basically includes a multi-link structural body in which a plurality of links is coupled together by a joint unit. The computational condition setting unit sets a motion purpose and a constraint condition of the multi-link structural body in an operation space describing inertia of force acting on the multi-link structural body and acceleration of the multi-link structural body in generalized inverse dynamics. Then, the computation unit calculates a virtual force that acts on the operation space to implement the operation space acceleration indicating the motion purpose, on the basis of a motion equation relating to the operation space including a term of an operation space bias acceleration in consideration to gravity compensation according to the inclination information, converts the virtual force to a real force in consideration to the constraint condition, and calculates a torque command value for driving the joint unit on the basis of the real force.

Furthermore, the computation unit corrects a torque target value calculated on the basis of a logical response model according to the real force and external torque acting on the joint unit in such a manner that the joint unit does not deviate from the logical response model, by using disturbance torque of the joint unit to calculate the torque command value. The computation unit can estimate torque acting on the joint unit from an angular velocity of the joint unit, and estimate the disturbance torque on the basis of a difference between the estimated torque and the torque command value.

Furthermore, a second aspect of the technique disclosed herein is a control method for controlling a surgical arm device. The control method includes: an inclination information acquisition step of acquiring inclination information of the surgical arm device; a setting step of setting a computational condition including gravity compensation according to the inclination information; and a computation step of calculating a command value to the surgical arm device according to the computational condition.

Furthermore, a third aspect of the technique disclosed herein is a surgical arm system that includes: a multi-link structural body in which a plurality of links is coupled by a joint unit; an inclination information acquisition unit that acquires inclination information of the multi-link structural body; a joint state detection unit that detects a state of the joint unit; and a drive control unit that controls driving of the joint unit according to a command value calculated depending on the inclination information and the state of the joint unit.

Effects of the Invention

According to the technique disclosed herein, it is possible to provide a control system and a control method for controlling a surgical arm device of a multi-link structure in which a plurality of links is coupled together by a joint unit in a force control mode, and a surgical arm system.

Note that effects described herein are mere examples and the effects of the present invention are not limited to them. Furthermore, in some cases, the present invention may further have other effects additional to the foregoing ones.

Other objects, features, and advantages of the technique disclosed herein will be clarified by more detailed descriptions of embodiments below and the accompanying drawings.

BRIEF DESCRIPTION OF DRAWINGS

FIG. 9 is a diagram illustrating a functional configuration of a control system 900 of the surgical arm device 100 that implements a force control using generalized inverse dynamics computation.

MODE FOR CARRYING OUT THE INVENTION

Hereinafter, embodiments of the technique disclosed herein will be described with reference to the drawings.

Figure 1:
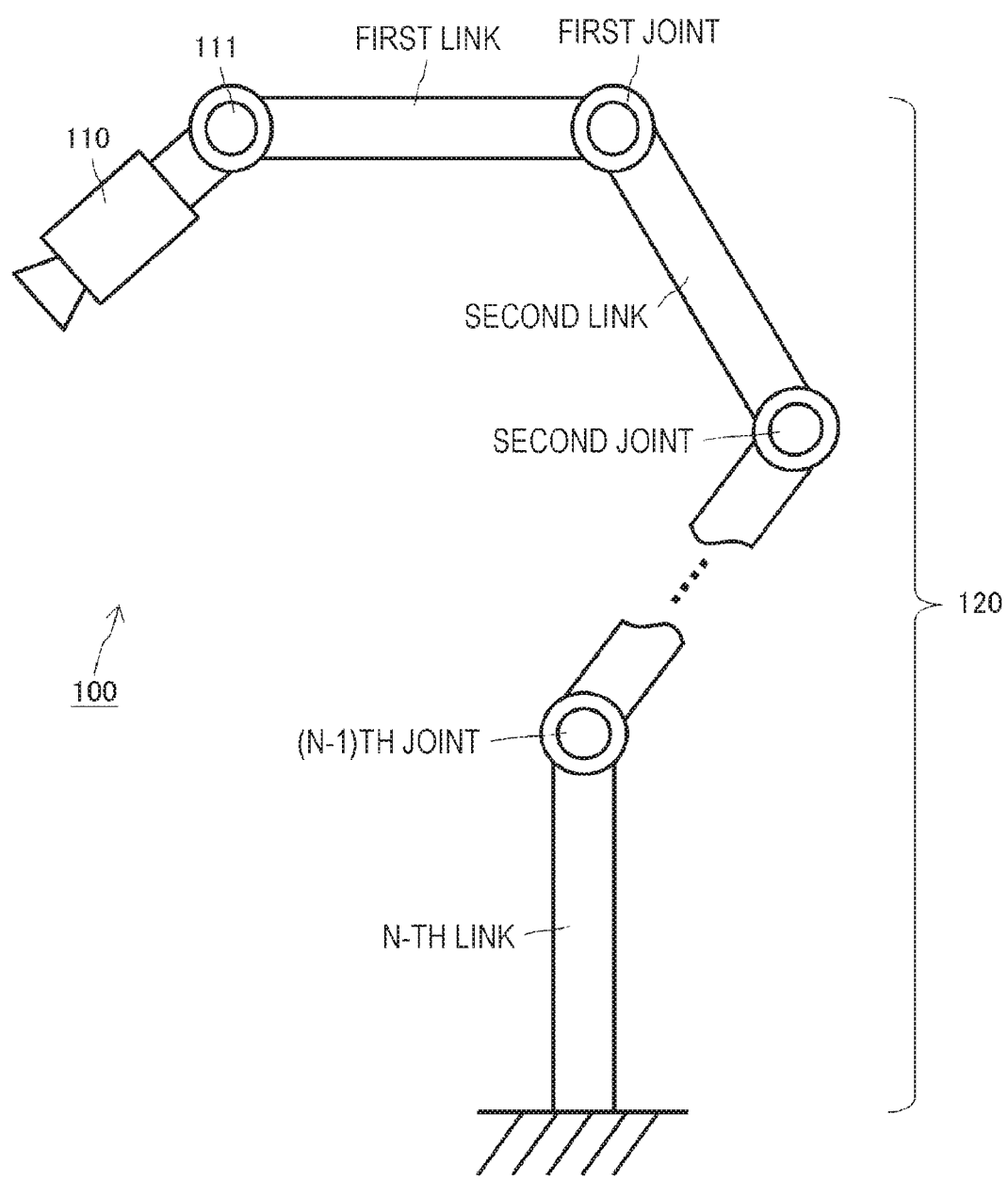
FIG. 1 is a diagram schematically illustrating a configuration example of a surgical arm device 100.

FIG. 1 schematically illustrates a configuration example of a surgical arm device 100 to which the technique disclosed herein is applicable. The surgical arm device 100 illustrated in the drawing includes a surgical arm 120 with an end effector 110 attached to a tip. The surgical arm device 100 is a medical or surgical robot used for operations under an endoscope on abdominal cavity or chest cavity, for example, which acts as a slave in a master-slave system.

The surgical arm 120 includes a multi-link structural body in which a plurality of links is coupled by joint units. The links can be dynamically handled as rigid bodies. The number of axes (or the number of joints) of the surgical arm 120, the degrees of freedom of the axes, and the number of links (or the number of arms) can be arbitrarily set. However, a medical or surgical arm has six or higher degrees of freedom, for example. For convenience, the links included in the surgical arm 120 illustrated in FIG. 1 will be called a first link, a second link, . . . , in sequence from the proximity of a distal end (or a rear end of the end effector 110). Furthermore, the joints included in the surgical arm 120 will be called a first joint, a second joint, . . . , in sequence from the proximity of the distal end (or the rear end of the end effector 110).

The end effector 110 is attached to the distal end of the surgical arm 120 with a wrist joint 111 therebetween. The end effector 110 includes various surgical instruments such as a lens tube of an endoscope, a probe of an ultrasonic inspection device, surgical tools such as a surgical knife and forceps, a pneumoperitoneum tube, an energy treatment tool, tweezers, and a retractor. The end effector 110 may be configured as a detachable end effector 110 such that the end effector 110 is attached to the distal end of the surgical arm 120 with changes in surgical instruments. In an endoscopic surgical operation, instead of making an incision in the abdominal wall to open the abdominal cavity, the abdominal wall is punctured with a plurality of cylindrical opening devices called trocars and the end effector 110 is inserted into the body cavity of the patient from the trocars (not illustrated).

Figure 2:
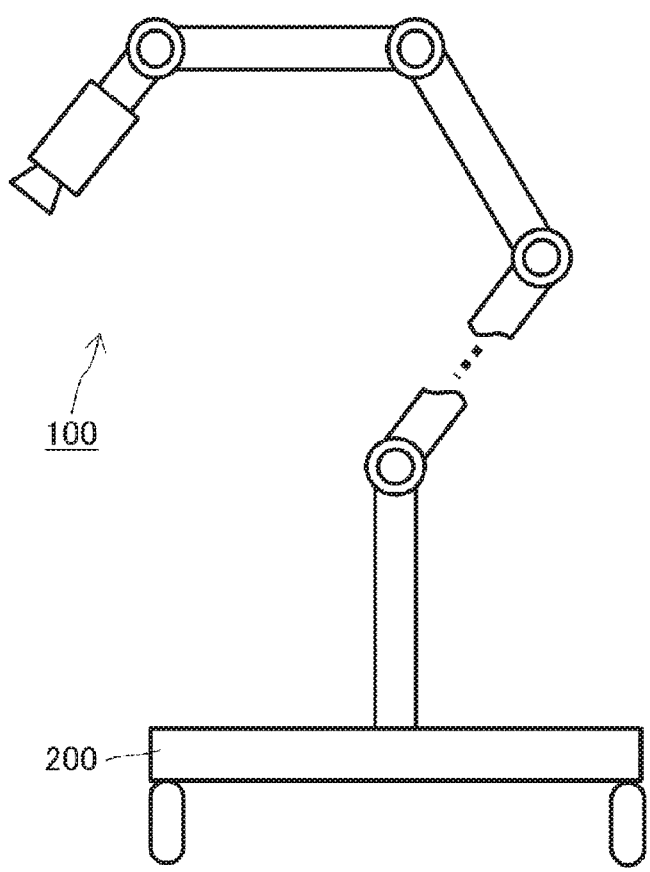
FIG. 2 is a diagram illustrating a state in which the surgical arm device 100 is mounted on a carriage 200.
Figure 3:
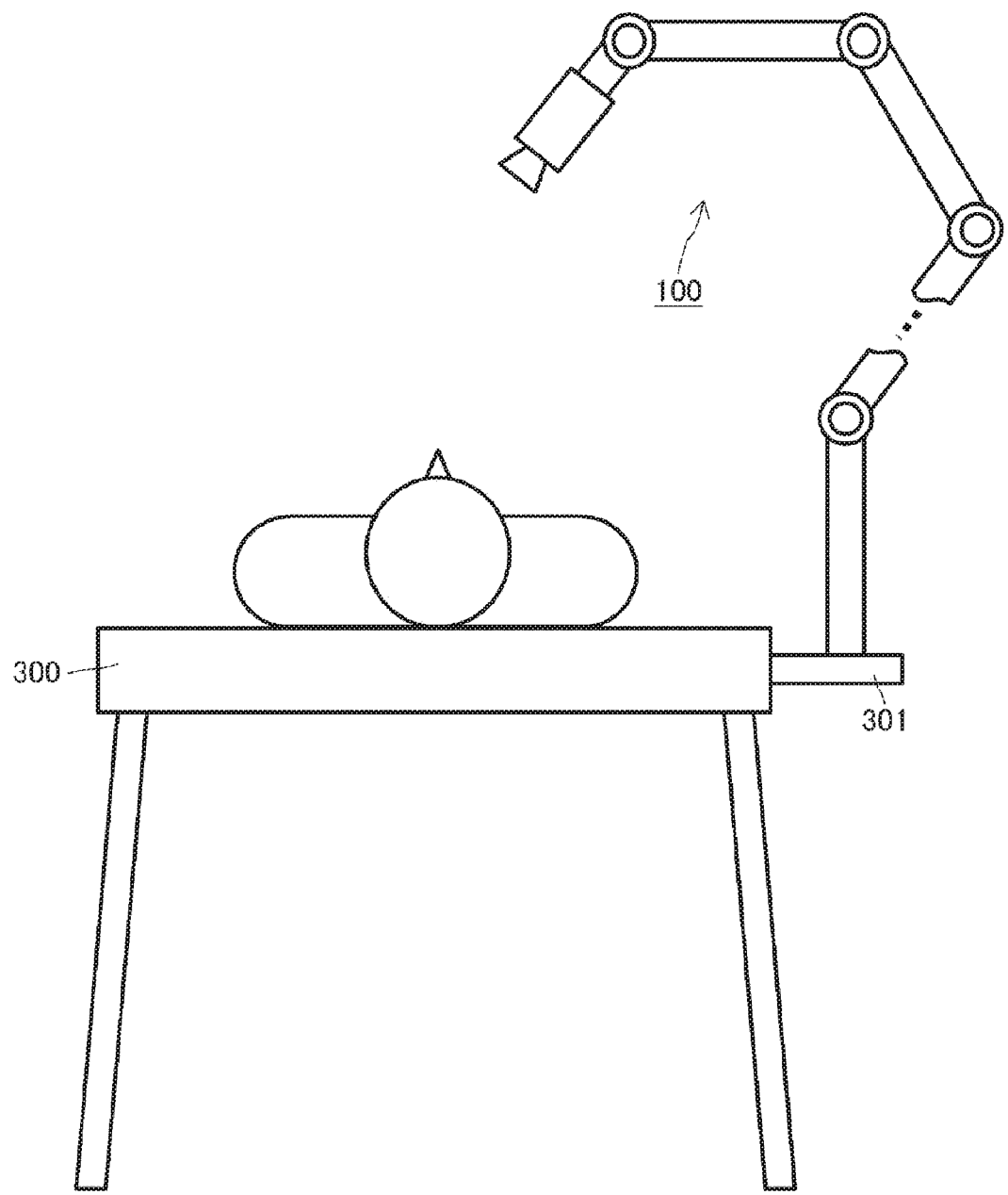
FIG. 3 is a diagram illustrating a state in which the surgical arm device 100 is attached to an operating table 300.

The surgical arm device 100 is assumed to be used in various forms such as being installed on the floor surface of a working space such as an operating room illustrated in FIG. 1, being mounted on a carriage 200 with casters for mobile use as illustrated in FIG. 2, or being attached to a side edge portion 301 of the operating table 300 as illustrated in FIG. 3.

For example, there is known an automated endoscopic system for optimal positioning (AESOP) device in which a surgical arm is attached to an operating table and a rigid endoscope is attached to the distal end of the arm, so that the operator controls the motion of the endoscope by voice through the head microphone.

Figure 4:
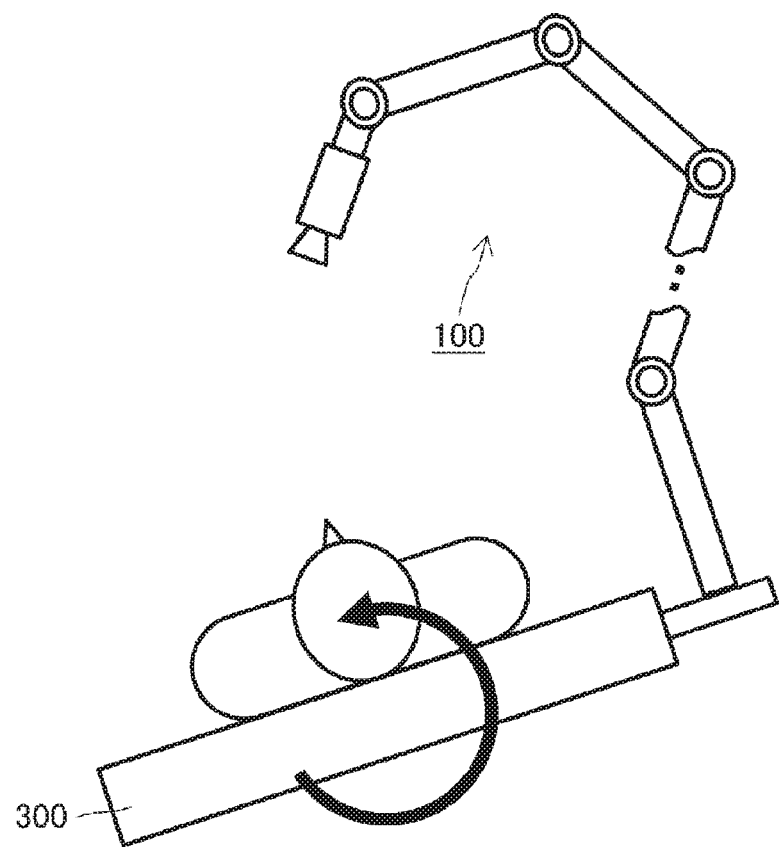
FIG. 4 is a diagram illustrating a state in which the operating table 300 with the surgical arm device 100 is inclined around a yaw.
Figure 5:
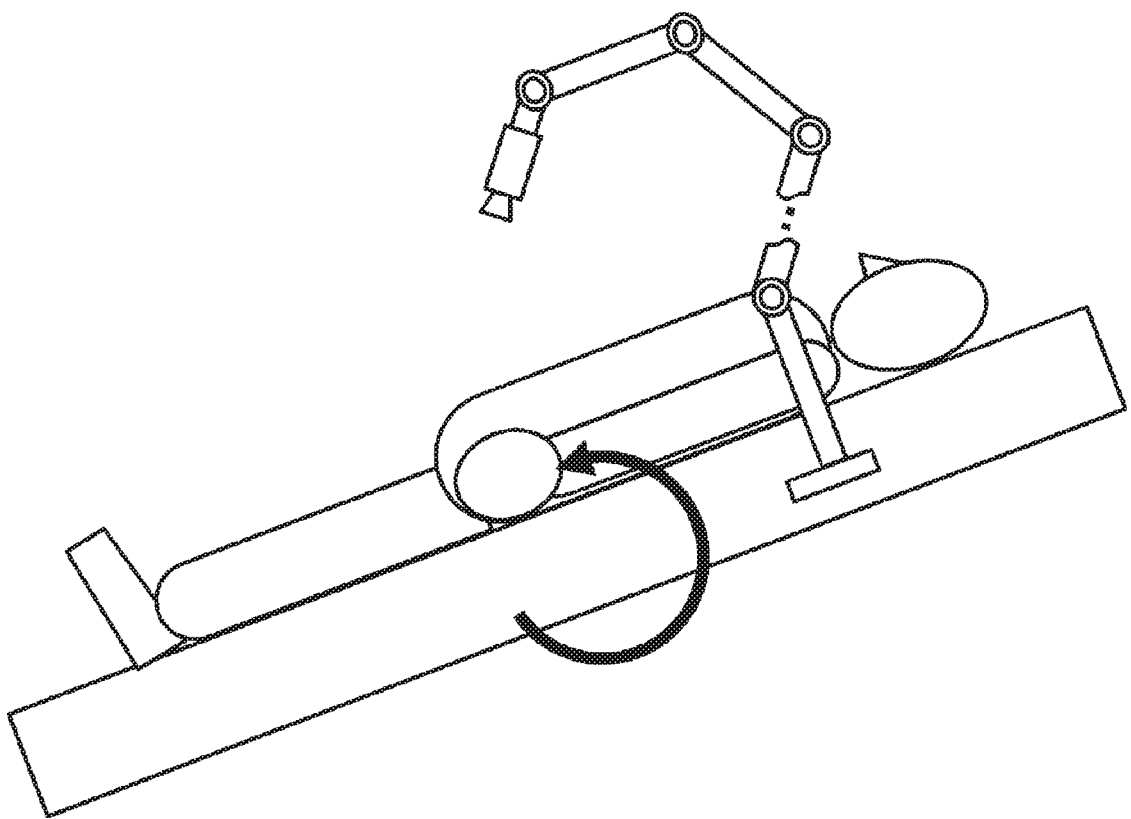
FIG. 5 is a diagram illustrating a state in which the operating table 300 with the surgical arm device 100 is inclined around a pitch.

Moreover, there has been provided an operating table that has a patient support surface of the operating table 300 rotatable around a yaw or a pitch (for example, refer to Patent Document 2). In a case where the surgical arm device 100 is attached to such a movable operating table 300, the surgical arm device 100 is inclined along with the operating table 300 (or the patient support surface) as illustrated in FIGS. 4 and 5. As a result, a Z-axis direction in a local coordinate system changes along with the inclination of the operating table 300 (or the patient support surface), so that the gravity force acting on the surgical arm 120 may not always coincide with the Z direction in the local coordinate system.

On the other hand, control methods of the joint units of the surgical arm 120 include position control and force control. In the present embodiment, the surgical arm 120 is controlled in a force control mode from the viewpoint of using the surgical arm device 100 for medical purposes and implementing interpersonal physical interactions.

Here, in the force control system, a resilient force acts on the surgical arm due to gravity force (the surgical arm's own weight) depending on the surgical arm's posture. Accordingly, it is general to provide the surgical arm with a mechanism for canceling out the surgical arm's own weight or perform "gravity compensation" by computing force necessary for surmounting the gravity force in the current posture of the surgical arm and adding the computing result to a command signal.

However, in a case where the operating table 300 to which the surgical arm device 100 is attached is inclined, the surgical arm 120 may not execute expected actions because the gravity compensation mechanism acted on the surgical arm 120 in a direction different from the direction of the gravity force or the force computed using a direction different from the direction of the gravity force was added to the command signal. If the gravity compensation acts on the surgical arm 120 in a direction different from the direction of the gravity force, the operator cannot obtain a light operational feeling, or the surgical arm 120 becomes unbalanced and starts to move in an unexpected direction. In particular, in the surgical arm device 100 for medical purposes, the end effector 110 of the surgical arm 120 is inserted and used in the body cavity of a patient (as described above), and thus an accident may occur unless the position of the end effector 110 and the generated force are coincident with specified values.

Thus, there is proposed herein a control system that computes force for gravity compensation on the basis of the correct direction of the gravity force according to the inclination of the surgical arm device 100 and implements an appropriate force control.

Figure 6:
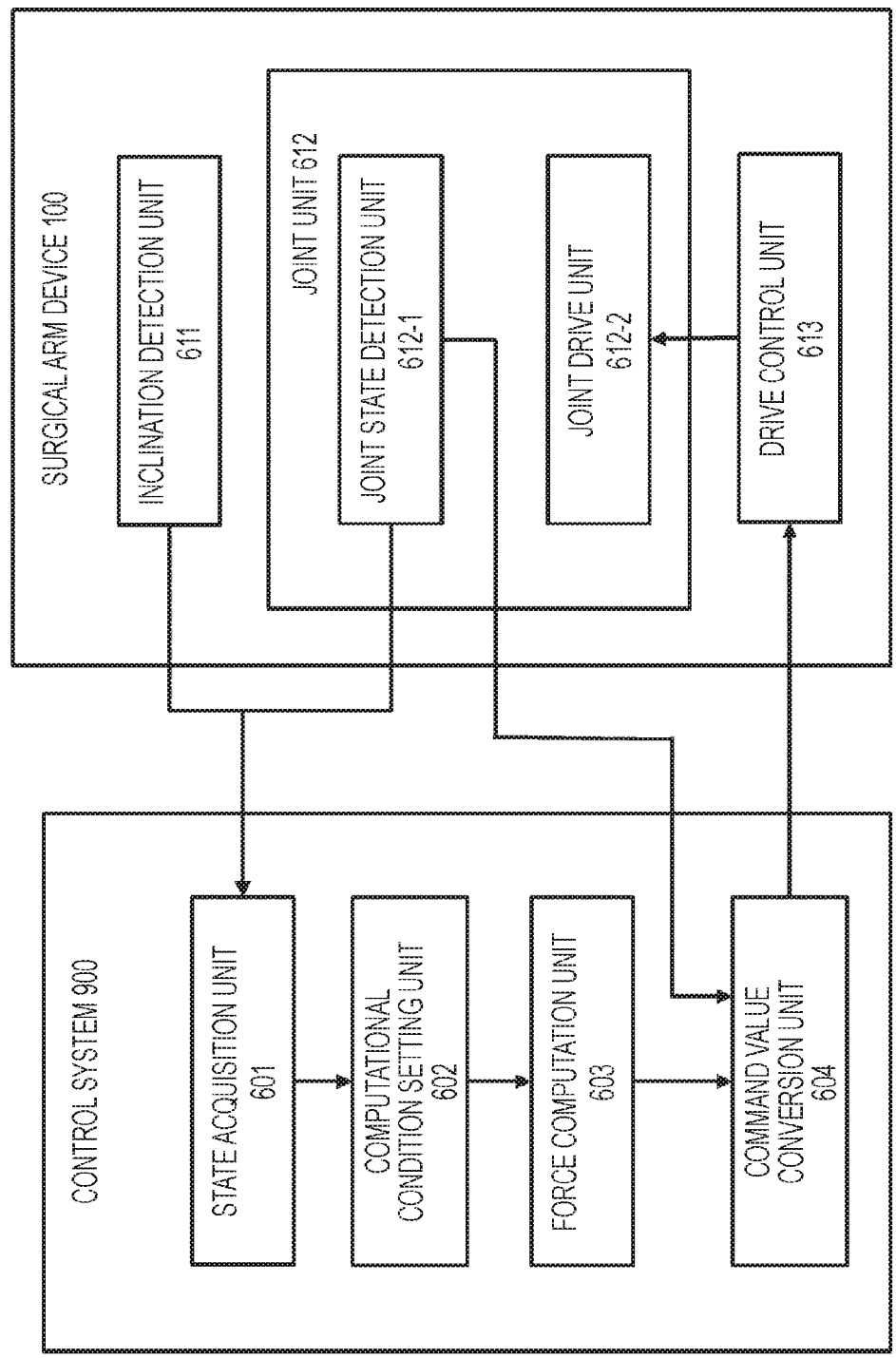
FIG. 6 is a diagram illustrating a functional configuration of a control system 600 of the surgical arm device 100.

FIG. 6 schematically illustrates a functional configuration of a control system 600 controlling the surgical arm device 100 in the force control mode. The control system 600 illustrated in the drawing includes a state acquisition unit 601, a computational condition setting unit 602, a force computation unit 603, and a command value conversion unit 604.

The state acquisition unit 601 acquires the state of the surgical arm device 100. In a general control system in the force control mode, force information such as torque generated at the joint units and positional information such as joint angles of the joint units are acquired as feedback information from a control target. In the present embodiment, the state acquisition unit 601 acquires an inclination angle of the surgical arm device 100 main body in addition to the force information and the positional information of the surgical arm 120.

On the basis of the information acquired by the state acquisition unit 601, the computational condition setting unit 602 sets computational conditions of a calculation formula for calculating force to be generated at the joint units of the surgical arm 120 (for example, the dynamic equation of the surgical arm 120) and forms the calculation formula. The calculation formula includes a gravity compensation term. In the present embodiment, the gravity compensation term for the correct direction of the gravity force is set as a computational condition according to the current inclination angle of the surgical arm device 100 main body acquired from the state acquisition unit 601.

The force computation unit 603 solves the calculation formula according to the computational conditions set by the computational condition setting unit 602 to calculate the force to be generated at the joint units of the surgical arm 120. The computational conditions set by the computational condition setting unit 602 include the gravity compensation term for the correct direction of the gravity force according to the inclination angle of the surgical arm device 100 main body. Therefore, in the present embodiment, the force computation unit 603 can perform appropriate gravity compensation to the correct direction of the gravity force according to the inclination angle of the surgical arm device 100 main body to calculate the force to be generated at the joint units. Note that the present embodiment assumes that the driving of the plurality of joint units provided in the surgical arm device 100 is controlled by whole body cooperative control using generalized inverse dynamics described later.

The command value conversion unit 604 converts the force information calculated by the force computation 603 to a command value for controlling the joint units of the surgical arm 120 and outputs the same to the surgical arm device 100. Note that the present embodiment assumes that an ideal joint control is applied to the drive control of the joint units such that an ideal response to a command value is implemented by correcting influence of disturbance.

In the surgical arm device 100, a drive control unit 613 controls driving of a joint drive unit 612-2 (such as an actuator) of joint units 612 constituting the surgical arm 120 according to the command value received from the control system 600. Although the surgical arm 120 is a multi-link structural body including a plurality of joint units and a plurality of links, FIG. 6 illustrates only a single joint unit 612 for the sake of simplification. It is to be understood that the other joint units not illustrated are configured in a similar manner. The joint unit 612 rotatably couples between the links in the surgical arm 120 and drives the surgical arm 120 by control of the rotational driving by control from the drive control unit 613.

A joint state detection unit 612-1 detects the state of the joint unit 612 such as the rotation angle of the joint unit 612 and the torque generated at the joint unit 612 and outputs the same to the state acquisition unit 601 of the control system 600.

An inclination detection unit 611 detects the inclination angle of the surgical arm device 100 or the surgical arm 120 and outputs the same to the state acquisition unit 601 of the control system 600. As illustrated in FIGS. 4 and 5, in a case where the surgical arm device 100 is attached to a movable operating table, the inclination angle of the surgical arm device 100 changes along with the operating table and the inclination detection unit 611 detects the inclination angle. Note that the surgical arm device 100 may not include the inclination detection unit 611 but the operating table 300 may include the inclination detection unit 611 so that the state acquisition unit 601 acquires the information regarding the inclination angle of the patient support surface from the operating table 300 integrated with the surgical arm device 100.

Subsequently, the overview of generalized inverse dynamics for use in the whole body cooperative control of the surgical arm device 100 according to the present embodiment will be provided.

The generalized inverse dynamics are basic computations in the whole body cooperative control of a multi-link structural body in which a plurality of links is coupled together by a plurality of joint units (for example, the surgical arm 120). By the basic computations, motion purposes relating to various dimensions in various operation spaces are converted to torque to be generated at the plurality of joint units in consideration to various constraint conditions.

The operation space here is an important concept in the force control of the surgical arm device. The operation space refers to a space for describing the relationship between the force acting on the multi-link structural body and the acceleration of the multi-link structural body. When controlling driving of the multi-link structural body by force control, not by positional control, the concept of an operation space is necessary to use the relationship between the multi-link structural body and the environment as a constraint condition. Examples of operation spaces include a joint space, a Cartesian space, and a momentum space to which the multi-link structural body belongs.

Furthermore, the motion purposes here refer to the target values in the driving control of a multi-link structural body, which correspond to the target values of the position, speed, acceleration, force, and impedance of the multi-link structural body to be attained by the driving control, for example.

Furthermore, the constraint conditions here refer to constrain conditions relating to the position, speed, acceleration, and force of a multi-link structural body determined by the shape and structure of the multi-link structural body, the surrounding environments of the multi-link structural body, and the settings made by the user. Examples of the constraint condition include information regarding generated force, priority, the presence or absence of an undriven joint, vertical reaction, friction weight, support polygon, and the like.

In generalized dynamics, to ensure both the stability of numerical calculations and the efficiency of computations capable of real-time processing, the arithmetic algorithm includes a virtual force calculation process in a first stage and a real force calculation process in a second stage. In the virtual force calculation process in the first stage, a virtual force to act on the operation space necessary for attainment of each motion purpose is determined in consideration to the priority of the motion purpose and the maximum value of the virtual force. In the following real force calculation process in the second stage, the virtual force obtained as described above is converted to a real force capable of being implemented by an actual configuration of a multi-link structural body including a joint force or an external force in consideration to constraints relating to a undriven joint, vertical reaction, friction weight, support polygon, and the like.

Here, the virtual force process in the first stage will be described.

A vector including a certain physical amount at each of the joint units of the multi-link structural body will be called generalized variable q (also called joint value q or joint space q). An operation space x is defined by the following equation (1) using a time derivative value and Jacobian J of the generalized variable q:

[Equation 1]

$$\dot{x}=J\dot{q} \quad (1)$$

In the surgical arm device 100 according to the present embodiment, for example, q corresponds to the rotation angle of each of the joint units constituting the surgical arm 120. The momentum equation relating to the operation space x of an overall link structure such as the surgical arm 120 can be expressed as shown in the following equation (2):

[Equation 2]

$$\tau=H\ddot{q}+b-J^T f \quad (2)$$

In the foregoing equation (2), $\tau$ represents a generalized force corresponding to the generalized variable q, b represents gravity force, Coriolis' force, and centrifugal force, and f represents an external force acting on the operation space. Furthermore, H represents an inertia matrix to the joint space of the entire structure, that is, a joint space inertia matrix. The foregoing equation (2) is deformed as in the following equation (3):

[Equation 3]

$$\ddot{x}=\Lambda^{-1}f+c \quad (3)$$

In the foregoing equation (3), $\Lambda^{-1}$ is called an operation space inertia inverse matrix. The operation space inertia inverse matrix $\Lambda^{-1}$ is expressed as in the following equation (4) using Jacobian J and the joint space inertia matrix H:

[Equation 4]

$$\Lambda^{-1}=JH^{-1}J^T \quad (4)$$

Furthermore, c in the third term of the right side of the foregoing equation (3) corresponds to an operation space bias acceleration, that is, an acceleration acting on the operation space without action of an external force. The operation space bias acceleration is expressed as in the following equation (5):

[Equation 5]

$$c=JH^{-1}(\Sigma-b)+\dot{J}\dot{q} \quad (5)$$

In the foregoing equation (5), b corresponds to gravity force, Coriolis' force, and centrifugal force (as described above). In the present embodiment, it is assumed that the surgical arm device 100 is attached to the movable operating table 300 and its inclination angle dynamically changes (refer to FIGS. 4 and 5). Therefore, gravity force g, Coriolis' force, and centrifugal force v is a function of the joint angle q or the joint angular velocity, b is expressed as in the following equation (6): Furthermore, the operation space bias acceleration c can be rewritten as in the following equation (7): According to the configuration of the control system 600 illustrated in FIG. 6, the joint angle q detected by the inclination detection unit 611 is acquired by the state acquisition unit 601.

[Equation 6]

$$b=v(q,\dot{q})-g(q) \quad (6)$$

[Equation 7]

$$c=JH^{-1}(\tau-v(q,\dot{q})+g(q))+\dot{J}\dot{q} \quad (7)$$

In generalized inverse dynamics, it is known that the motion purposes of the position and the speed relating to the operation space x can be expressed as an acceleration in the operation space x. In this case, to implement the operation space acceleration as a target value given as a motion purpose from the foregoing equation (1), the virtual force $f_v$ to act on the operation space x is obtained by solving a kind of linear complementary problem as in the following equation (8):

[Equation 8]

$$w+\ddot{x}=\Lambda^{-1}f_v+c \quad (8)$$

$$\text{subject to} \begin{cases} ((w_i<0) \cap (f_{v_i}=U_i)) \cup \\ ((w_i>0) \cap (f_{v_i}=L_i)) \cup \\ ((w_i=0) \cap (L_i<f_{v_i}<U_i)) \end{cases}$$

In the second term of the left side of the foregoing equation (8), an operation space bias acceleration c including the gravity compensation term for the correct direction of the gravity force is used according to the current inclination angle of the surgical arm device 100 main body acquired from the state acquisition unit 601 as illustrated in the foregoing equation (7). Consequently, it is to be understood that the virtual force $f_v$ to which appropriate gravity compensation to the correct direction of the gravity force is applied can be determined by solving the foregoing equation (8).

Here, in the foregoing equation (8), $L_i$ and $U_i$ respectively represent the negative lower limit value of an i-th component of $f_v$ (including $-\infty$) and the positive upper limit value of the i-th component of $f_v$ (including $+\infty$). The linear complementary problem can be solved by Iterative method, Pivot method, or a method to which robust acceleration control is applied, for example.

Note that calculating the operation space inertia inverse matrix $\Lambda^{-1}$ and the bias acceleration c as in the foregoing equations (4) and (5) as definitional equations would take a large calculation cost. Accordingly, there has been proposed a method by which to perform the calculation process of the operation space inertia inverse matrix $\Lambda^{-1}$ at a higher speed by application of forward dynamics (FWD) to obtain a generalized acceleration (joint acceleration) from the generalized force (joint force $\tau$) of the multi-link structural body. Specifically, by using forward dynamic computations, the operation space inertia inverse matrix $\Lambda^{-1}$ and the bias acceleration c can be calculated from information regarding the forces acting on the multi-link structural body such as the joint space q, the joint force $\tau$, and the gravity force g. In this manner, applying the forward dynamic computations relating to the operation space makes it possible to calculate the operation space inertia inverse matrix $\Lambda^{-1}$ by a calculation amount of O(N) to the number N of the joint units.

In the control system 600 illustrated in FIG. 6, at the calculation of the operation space inertia inverse matrix $\Lambda^{-1}$, the information regarding the forces acting on the surgical arm device 100 as a multi-link structural body (the joint space q, the joint force $\tau$, and the gravity force g) is acquired from the joint state detection unit 612-1 and the inclination detection unit 611. It is to be understood that the information regarding the correct direction of the gravity force can be obtained on the basis of the inclination angle from the inclination detection unit 611 according to the inclination angle of the operating table 300 to which the surgical arm device 100 is attached.

As an example of setting a motion purpose, the condition for attaining the target value of the operation space acceleration (represented by second-order differentiation of x with a superscript bar) by a virtual force $f_{vi}$ of an absolute value $F_i$ or less can be expressed by the following equation (9):

[Equation 9]

$$L_i = -F_i, U_i = F_i, \ddot{x}_i = \ddot{\bar{x}}_i \quad (9)$$

Furthermore, as described above, the motion purpose relating to the position and speed of the operation space x can be represented as a target value of the operation space acceleration, and specifically, can be represented by the following equation (10) (where the target values of the position and speed of the operation space x are represented by x and first-order differentiation of x with a subscript bar).

[Equation 10]

$$\ddot{\bar{x}}_i = K_p(\bar{x}_i - x_i) + K_v(\dot{\bar{x}}_i - \dot{x}_i) \quad (10)$$

Besides, using a concept of a decomposition operation space makes it possible to set motion purposes relating to an operation space represented by the linear sum of other operation spaces (momentum, Cartesian relative coordinates, interlocking joints, and others). Note that the competing motion purposes need to be given priorities. The linear complementary problems can be solved in order of each priority or from lower priorities, and the virtual force obtained from the preceding linear complementary problem can act on the following linear complementary problem as known external force.

Subsequently, the real force calculation process in the second stage will be described.

The virtual force $f_v$ obtained as described above is converted to a real joint force and an external force. The condition for attaining a generalized force $\tau_v(=J_v^T f_v)$ from the virtual force by torque $\tau_a$ and an external force $f_e$ generated at the joint units is expressed by the following equation (11):

[Equation 11]

$$\begin{bmatrix} J_{vu}^T \\ J_{va}^T \end{bmatrix}(f_v - \Delta f_v) = \begin{bmatrix} J_{eu}^T \\ J_{ea}^T \end{bmatrix} f_e + \begin{bmatrix} 0 \\ \tau_a \end{bmatrix} \quad (11)$$

In the foregoing equation, the index a represents an assembly of drive joint units (drive joint assembly) and the index u represents an assembly of non-drive joint units (non-drive joint assembly). In other words, the upper stage of the foregoing equation (11) represents the balance between forces in the space by the non-drive joint units (non-drive joint space), and the lower stage of the same represents the balance between forces in the space by the drive joint units (drive joint space). The signs $J_v^u$ and $J_{va}$ respectively represent a non-drive joint component and a drive joint component of Jacobian relating to the operation space on which the virtual force $f_v$ acts. The signs $J_{eu}$ and $J_{ea}$ respectively represent a non-drive joint component and a drive joint component of Jacobian relating to the operation space on which the external force $f_e$ acts. Furthermore, the sign $\Delta f_v$ represents a component of the virtual force $f_v$ incapable of being attained by the real force.

The upper stage of the foregoing equation (11) is indeterminate, and solving a quadratic programming problem as shown in the following equation (12), for example, makes it possible to obtain $f_e$ and $\Delta f_v$.

[Equation 12]

$$\min \tfrac{1}{2}\varepsilon^T Q_1 \varepsilon + \tfrac{1}{2}\xi^T Q_2 \xi$$

subject to $U\xi \geq v$ \quad (12)

In the foregoing equation (12), the symbol $\varepsilon$ represents a variable vector on the upper stage of the foregoing equation (11). The symbols Q1 and Q2 represent positive definite symmetric matrixes indicating the weights for minimization. Furthermore, the inequality constraint in the foregoing equation (12) is used to represent constraint conditions relating to external force such as vertical reaction, friction cone, maximum value of external force, and support polygon. For example, the inequality constraint relating to a rectangular support polygon is expressed by the following equation (13):

[Equation 13]

$$|F_x| \leq \mu_t F_z, |F_y| \leq \mu_t F_z, F_z \leq 0,$$

$$|M_x| \leq d_y F_z, |M_y| \leq d_x F_z, |M_x| \leq \mu_r F_z \quad (13)$$

where z represents the direction of normal to the contact surface, and x and y represent two orthogonal tangential directions perpendicular to z. $(F_x, F_y, F_z)$ and $(M_x, M_y, M_z)$ represent an external force and an external force moment acting on the contact point. $\mu_t$ and $\mu_r$ represent friction coefficients relating to translation and rotation, respectively. $(d_x, d_y)$ represents the size of the support polygon.

From the foregoing equations (12) and (13), solutions $f_e$ and $\Delta f_v$ of minimum norm or minimum error. Substituting $f_e$ and $\Delta f_v$ obtained from the foregoing equation (12) into the lower stage of the foregoing equation (11) makes it possible to obtain the joint force $\tau_a$ necessary for attaining the motion purpose.

In a system in which the basis is fixed and no undriven joint is provided, all the virtual forces can be replaced by only the joint force, and $f_e=0$, $\Delta f_v=0$ in the foregoing equation (11). In this case, the real joint force $\tau_a$ can be obtained from the lower stage of the foregoing equation (11) according to the following equation (14):

[Equation 14]

$$\tau_a = J_{va}^T f_v \qquad (14)$$

As described above, performing the virtual force calculation process and the real force calculation process in sequence using the generalized inverse dynamics makes it possible to obtain the joint force $\tau_a$ for attaining the desired motion purpose. In reverse, reflecting the joint force $\tau_a$ calculated using the generalized inverse dynamics on a logical model in the motion of the joint unit 612 of the surgical arm device 100 makes it possible to drive the joint units 612 to attain the desired motion purpose in the force control mode.

Furthermore, in the present embodiment, in the process of calculating the joint force $\tau_a$ (more strictly, the process of calculating the virtual force), the force generated at the joint units can be calculated by performing appropriate gravity compensation to the correct direction of the gravity force on the basis of the inclination angle of the surgical arm device 100 main body detected by the inclination detection unit 611.

Note that, for details of the whole body cooperative control using the generalized inverse dynamics described so far, in particular, the process of deriving the virtual force $f_v$, the method for determining the virtual force $f_v$ by solving the foregoing linear complementary problems, and the method for solving the secondary planning problem, refer to, for example, Japanese Patent Application Laid-Open No. 2009-95959 and Japanese Patent Application Laid-Open No. 2010-188471 already transferred to the applicant of the present application.

Subsequently, an ideal joint control applied to the drive control method of the joint units in the present embodiment will be described.

According to the joint force command value $\tau_a$ determined by the computation using the generalized inverse dynamics described above, the actuator driving the joint unit 612 is controlled in the force control mode.

Figure 7:
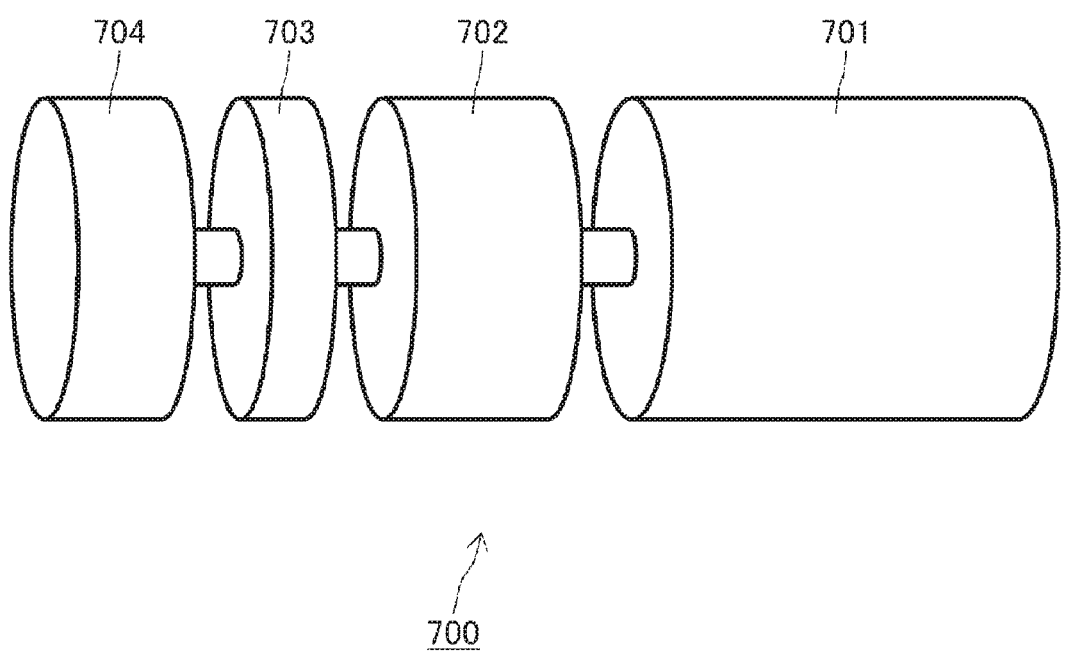
FIG. 7 is a diagram illustrating a configuration example of an actuator 700.

FIG. 7 illustrates a configuration example of an actuator 700 driving the joint unit 612. The actuator 700 illustrated in the drawing includes a motor for generating rotation torque (for example, DC brushless motor) 701 and a decelerator 702 for converting the rotation force of the motor 701 to a sufficient generative force. Furthermore, the actuator 700 also has an encoder 703 for measuring the joint angle and a torque sensor 704 for detecting the rotation torque attached to an output shaft of the decelerator 702. The encoder 703 and the torque sensor 704 correspond to the joint state detection unit 612-1 illustrated in FIG. 6. Note that, as the torque sensor 704, for example, the torque measurement device disclosed in Japanese Patent Application Laid-Open No. 2009-288198 already transferred to the applicant of the present application can be applied.

Performing the force control on the actuator 700 using the real force $\tau_a$ calculated by the computation using the generalized inverse dynamics for the joint force command value makes it possible to avoid the influence of disturbance. However, when the joint actuator makes a response deviating from a logical model for use in the dynamics computation, the desired motion state cannot be attained even with the action of the torque calculated by the dynamic computation on the actuator.

In actuality, the actuator 700 having the decelerator 702 as illustrated in FIG. 7 includes dynamics parameters such as friction and inertia making difficult modeling and identification, which become a main cause of disturbance affecting the force control. Unless any measure is taken on the problem with disturbance, the force control will easily deviate from the logical model. In other words, it is further necessary to use an ideal actuator in the joints such that the friction and inertia of the joint unit becoming the main cause of error coincide with the logical model.

Accordingly, in the present embodiment, a method for correcting the responses of the actuator 700 according to the logical model even under the influence of disturbances such as friction and inertia incapable of modeling is used to perform a drive control with the joint unit 612 as ideal joint. Hereinafter, a method of ideal joint control for the actuator 700 driving the joint unit 612 to make responses according to the logical model will be described.

In the dynamics computation of the surgical arm device 100 (or the surgical arm 120), the actuator 700 is modeled by a motion equation of a second-order delay system as shown in the following equation (15):

[Equation 15]

$$I_a \ddot{q} = \tau_a + \tau_e - v_a \dot{q} \qquad (15)$$

In the foregoing equation (15), $I_a$ represents inertia moment of joint (virtual inertia), q represents the joint angle of the joint (obtained as output of the encoder 704), $\tau_a$ represents the command value of the generative torque at the joint, $\tau_e$ represents external torque acting on the joint, and $v_a$ represents a virtual viscosity coefficient of inside of the joint (unknown and difficult to model). The foregoing equation (15) can be also said to be a logical model indicating the motion of the actuator 700.

By the computation using the generalized inverse dynamics described above, the real force $\tau_a$ to act on the actuator 700 can be calculated according to the motion purpose and the constraint condition. Furthermore, ideally, the actuator 700 should make responses according to the logical model illustrated in the foregoing equation (15) to attain the desired motion purpose.

In actuality, however, there may occur errors, that is, modeling errors between the motion of the actuator 700 and the logical model illustrated in the foregoing equation (15) due to the influence of disturbances such as friction and inertia incapable of modeling. The modeling errors are roughly divided into errors resulting from mass properties of a multi-link structural body such as weight, gravity center, and inertia tensor and errors resulting from friction and inertia in the inside of the actuator 700 in the multi-link structural body.

Among them, the former modeling errors resulting from the mass properties can be relatively easily reduced by increasing the accuracy of computer aided design (CAD) data and application of an identification method at the time of building of the logical model. On the other hand, the latter modeling errors resulting from friction and inertia in the inside of the actuator 700 are caused by phenomena such as friction in the decelerator 702 of the actuator 700, for example, that are difficult to model. Accordingly, the unignorable modeling errors may remain at the time of building of the logical model.

Furthermore, there may occur errors between the values of the inertia $I_a$ and the viscosity resistance coefficient $v_e$ in the foregoing motion equation (15) and the actual values of the actuator 700. The errors that are difficult to model may be disturbances in the drive control of the actuator 700.

Therefore, in actuality, the actuator 700 may not make responses according to the logical model illustrated in the foregoing equation (15) due to the influence of such disturbances. As a result, even if the real force $\tau_a$ is applied as the joint force calculated by generalized inverse dynamics to the actuator 700, the motion purpose as the control target cannot be attained.

Accordingly, in the present embodiment, there is considered a response correction method by which to add an active control system to the actuator 700 such that the actuator 700 makes an ideal response according to the logical model illustrated in the foregoing equation (15). Specifically, the present embodiment allows not only a friction-compensated torque control using the torque sensor 704 of the actuator 700 but also ideal responses according to the logical values of the inertia $I_a$ and the viscosity resistance coefficient $v_a$ to the required generated torque $\tau_a$ and external torque $\tau_e$.

Figure 8:
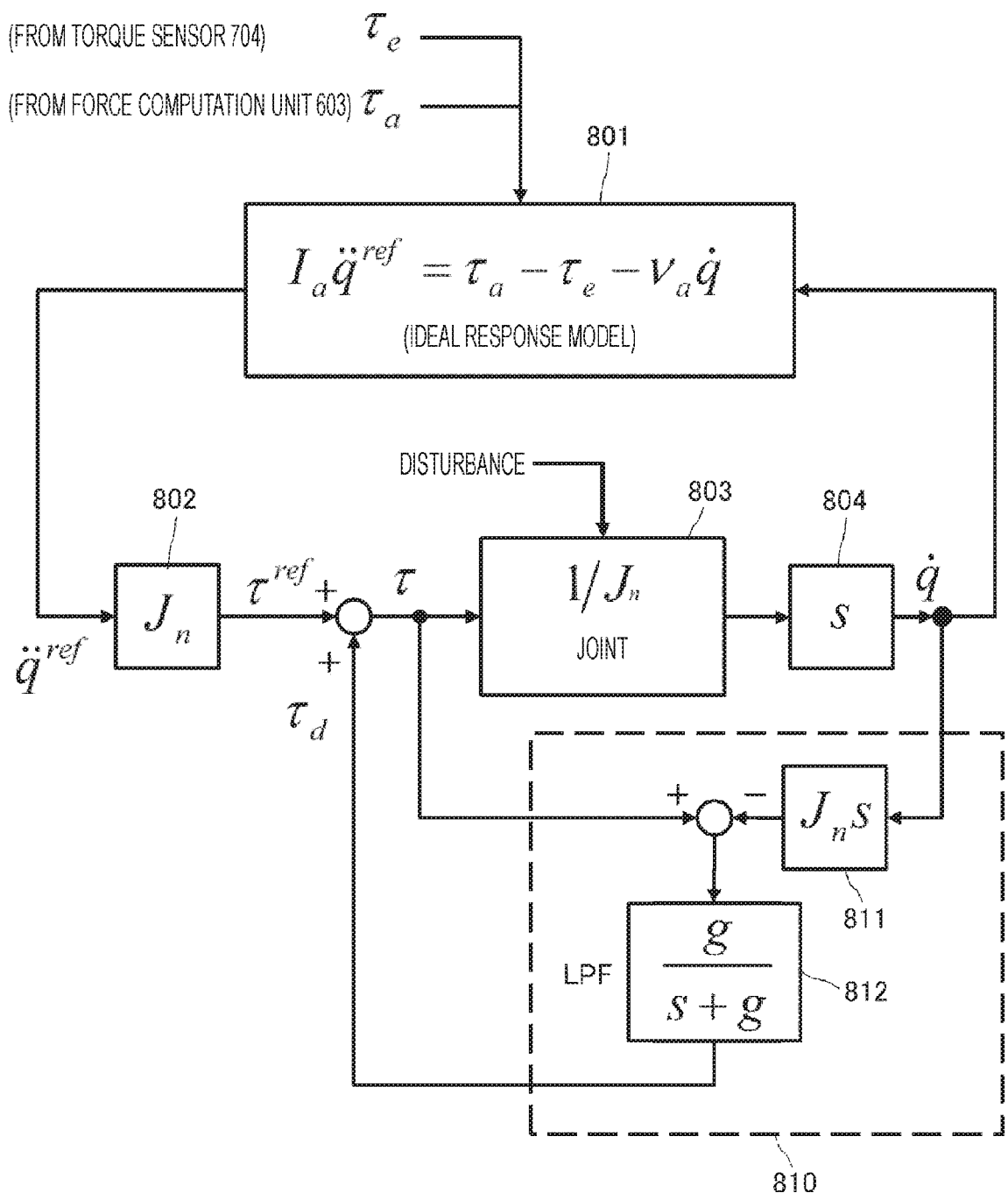
FIG. 8 is a diagram illustrating control blocks for the actuator 700 to make responses according to a logical model.

FIG. 8 is a control block diagram for the actuator 700 to make responses according to the logical model. The control block illustrated in the drawing corresponds to a process by the command value conversion unit 604 to correct the real force $\tau_a$ calculated by the force computation unit 603 for making ideal responses in the control system 600 illustrated in FIG. 6, for example.

In FIG. 8, the part surrounded by a dot line corresponds to a disturbance observer 810, which estimates disturbance torque $\tau_d$ to the actuator 700 and eliminates the influence on the control system to build a robust acceleration and control system. However, $J_n$ represents the nominal value of inertia in the joint, J represents the actual (unknown) value of inertia in the joint, and q represents the joint angle. Furthermore, the virtual inertia $I_a$ of the joint is assigned a virtual constant as a design matter in the dynamics computation.

The force computation unit 603 determines the torque command value $\tau_a$ to the actuator 700 by computation using the generalized inverse dynamics described above in each control cycle. Furthermore, the joint state detection unit 612-1 sends to the command value conversion unit 604 an external torque actual measurement value $\tau_e$, that is measured by the torque sensor 704 attached to the output shaft of the decelerator 702 of the actuator 700 and an angular velocity actual measurement value that is obtained from the joint angle q measured by the encoder 703 attached to the output shaft of the decelerator 702.

Reference number 801 represents a computing unit that performs computations according to the ideal response model expressed by the motion equation illustrated in the foregoing equation (15). The computing unit 801 receives the torque command value $\tau_a$, the external torque actual measurement value $\tau_e$, and the actual measurement value of the joint angular velocity (first-order differentiation of the joint angle q), calculates an acceleration of the joint angle q on the left side of the foregoing equation (15) (second-order differentiation of a joint angle target value $q^{ref}$), and inputs the calculated result as a joint angular acceleration target value to the disturbance observer 810.

Reference number 802 represents a computing unit that calculates torque generated at the actuator 700 on the basis of the rotation angular acceleration of the actuator 700. The computing unit 802 multiplies the acceleration target value of the joint angle q input to the disturbance observer 810 by the virtual inertia nominal value $J_n$ of the joint to convert the acceleration target value to the torque target value $\tau^{ref}$ in the present control cycle.

In the ideal response, the desired motion purpose should be attained by causing the actuator 700 to generate the torque target value $\tau^{ref}$. As described above, however, the actual responses may be placed under the influence of disturbances and others. Accordingly, in the present embodiment, the control block includes the disturbance observer 810 to estimate the disturbance torque $\tau_d$. Therefore, by performing a feedforward control in which to make a correction to the torque target value $\tau_{ref}$ in the present control cycle by the disturbance torque $\tau_d$ estimated by the disturbance observer 810 in the previous control cycle, the control block can obtain the torque command value $\tau$ to the joint in the present control cycle.

Reference number 803 represents the joint, which includes a transfer function $1/J_n$. When the joint 803 is subjected to a force control with the torque command value $\tau$, the joint 803 is rotationally driven under influence of disturbances such as friction and inertia. Specifically, the command value conversion unit 604 converts the torque command value $\tau$ to a current command value, which constitutes an instruction input to the drive control unit 613 (or the motor driver driving the motor 701).

The external torque $\tau_e$ generated at the joint and the joint angle q at the time of driving of the joint 803 are respectively measured by the torque sensor 704 and the encoder 703. Furthermore, reference number 804 represents a computing unit that performs differential operations and subjects the joint angle q measured by the encoder 703 to temporal differentiation to obtain the joint angular velocity. The joint angular velocity obtained here constitutes an input to the computing unit 801 (described above) that performs computations according to the ideal response model.

The disturbance observer 810 includes computing units each indicated with reference numbers 811 and 812. The computing unit 811 applies a transfer function $J_{ns}$ including the joint virtual inertia nominal value $J_n$ to the joint angular velocity output from the computing unit 804 to estimate the torque acting on the joint. Then, subtracting the torque estimated by the computing unit 811 from the torque command value $\tau$ in the present control cycle to the actuator 700 makes it possible to estimate the disturbance torque $\tau_d$. Furthermore, performing a feedforward control in which to make a correction to the torque target value $\tau^{ref}$ in the next control cycle of the disturbance torque obtained in the present control cycle makes it possible to obtain the torque command value $\tau$ to the joint in the next control cycle.

Furthermore, the computing unit 812 also constitutes a low pass filter (LPF) that is inserted in the course of outputting the estimated value of the disturbance torque $\tau_d$ for prevention of system divergence. The computing unit 812 performs the computation expressed by the transfer function $g/(s+g)$ to output only the low-frequency components to the input value to achieve stability in the system.

In this manner, even if there exist disturbance components incapable of modeling such as friction and inertia in the joint unit, the acceleration response of the actuator 700 can follow the acceleration target value. In other words, when the right side of the foregoing equation (15) is assigned, the joint angular acceleration on the left side is attained, and thus the actuator 700 can make responses according to the logical model even under the influence of disturbances. Note that, since the low pass filter $g/(s+g)$ 812 is inserted in the course of outputting the disturbance torque $\tau_d$ (as described above), this method is not suitable for eliminating disturbances in the high-frequency band.

According to the control block configuration illustrated in FIG. 8, in the drive control of the actuator 700, the response of the actuator 700 can follow the target value even with disturbance components such as friction and inertia. Furthermore, in the drive control of the joint unit 612, the actuator 700 can make ideal responses according to the inertia $I_a$ and the viscosity resistance coefficient $v_a$ assumed in the logical model.

Note that, for details of the ideal joint control, refer to Japanese Patent Application Laid-Open No. 2009-269102, which has already been transferred to the applicant of the present application, for example.

FIG. 9 is a diagram illustrating a functional configuration of a control system 900 of the surgical arm device 100 that implements a force control using generalized inverse dynamics computation.

The surgical arm device 100 to be controlled by the control system 900 includes an imaging unit as the end effector 110 of the surgical arm 120, an inclination detection unit 911, the surgical arm 120, and a drive control unit 913 that controls driving of a joint unit 912 of the surgical arm 120.

The imaging unit attached as the end effector 110 is a rigid endoscope that is inserted into the body cavity of a patient from a trocar during a surgery, for example. Specifically, the imaging unit is a camera or the like that captures an image of an imaging subject in the form of moving image or still image. The imaging unit has a plurality of light-receiving elements that is aligned two-dimensionally and acquires an image signal indicating an image of the body cavity of a patient as an imaging subject through photoelectric conversion by the light-receiving elements.

A display device 920 to display the image captured by the imaging unit may be externally connected to the surgical arm device 100 or the surgical arm device 100 may include the display device 920. The display device 920 is a device that displays various kinds of information in various forms such as text and image on a display screen. The display device 920 includes an image signal processing unit that performs various kinds of image processing on the image signal and a display drive unit that outputs and displays the image based on the processed image signal on the screen. In the present embodiment, the display device 920 displays the image captured by the imaging unit as the end effector 110 of the surgical arm 120 on the screen.

The inclination detection unit 911 detects the inclination angle of the surgical arm device 100 or the surgical arm 120. For example, as illustrated in FIGS. 4 and 5, in a case where the surgical arm device 100 is attached to a movable operating table, the inclination angle of the surgical arm device 100 dynamically changes along with the operating table and the inclination detection unit 911 detects the inclination angle. Note that the surgical arm device 100 may not include the inclination detection unit 911 but the operating table 300 may include the inclination detection unit 911 to acquire the information regarding the inclination angle of the patient support surface from the operating table 300 integrated with the surgical arm device 100. The inclination detection unit 911 transmits the detected inclination angle to the control system 900.

The Z-axis direction in the local coordinate system changes along with the inclination of the operating table 300 (or the patient support surface), so that the gravity force acting on the surgical arm 120 may not always coincide with the Z direction in the local coordinate system. In contrast to this, in the present embodiment, the direction of the gravity force acting on the surgical arm 120 is not fixed in the Z direction but the direction of the gravity force can be handled as a function of the inclination angle detected by the inclination detection unit 911.

The surgical arm 120 is a multi-link structural body having a plurality of joint units and a plurality of links, and includes the drive control unit 913 that controls driving of the joint units. Although the surgical arm 120 is a multi-link structural body including the plurality of joint units and the plurality of links, FIG. 9 illustrates only a single joint unit 912 for the sake of simplification. It is to be understood that the joint units not illustrated are configured in a similar manner. In other words, the plurality of joint units is controlled by the drive control unit 913 and driven within their respective movable range, whereby the position and posture of the imaging unit as the end effector 110 can be controlled.

The drive control unit 913 controls the amount of current to be supplied to the motor of the actuator for driving the joint unit 912, for example, to control the rotation number of the motor and control the rotation angle and generative torque of the joint unit 912. However, the drive control unit 913 performs the drive control of the joint unit 912 on the basis of the results of the computation by the control system 900. Therefore, the amount of current to be supplied by the drive control unit 913 to the actuator and motor of the joint unit 912 is basically determined under control of the control system 900.

The joint unit 912 rotatably couples between the links in the surgical arm 120 and drives the surgical arm 120 by control of the rotational driving by the drive control unit 913. The joint unit 912 includes a joint drive unit 912-2 and a joint state detection unit 912-1.

The joint drive unit 912-2 is a drive mechanism of the joint unit 912, which includes the motor of the actuator illustrated in FIG. 7, for example. The joint drive unit 912-2 is driven under control of the drive control unit 913, whereby the joint unit 912 is rotationally driven.

The joint state detection unit 912-1 detects the state of the joint unit 912 such as the rotation angle of the joint unit 912 and the torque generated at the joint unit 912. The joint state detection unit 912-1 includes the encoder 703 and the torque sensor 704 that are attached to the output shaft of the decelerator 702 of the actuator 700 illustrated in FIG. 7. The joint state detection unit 912-1 transmits the detected state of the joint unit 912 to the control system 900.

Meanwhile, the control system 900 includes a whole body cooperative control unit 930, an ideal joint control unit 940, an input unit 950, and a storage unit 960. The control system 900 includes various information processing devices externally connected to the surgical arm device 100 to be controlled, such as a personal computer (PC) and a server, for example. Alternatively, the control system 900 may be a device such as a controller mounted on the surgical arm device 100 to be controlled.

The input unit 950 is an input interface for the user to input information and orders regarding drive control of the surgical arm device 100 to the control system 900. Specifically, the input unit 950 includes operation devices such as a mouse, a keyboard, a touch panel, buttons, switches, a lever, a joy stick, and a pedal. For example, the driving of the surgical arm 120 is controlled according to the user's operation input to the input unit 950, whereby the position and posture of the imaging unit as the end effector 110 are controlled.

The storage unit 960 stores various kinds of information to be processed by the control system 900. In the present embodiment, the storage unit 960 can store various parameters for use in the whole body cooperative control of the surgical arm device 100 to be performed in the control system 900 and in computations relating to the ideal joint control of the joint units. For example, the storage unit 960 may store information regarding the motion purposes and constraint conditions to be used by a computational condition setting unit 932 in computations relating to the whole body cooperative control (described later). Furthermore, in the present embodiment, the storage unit 960 can store various kinds of arm information regarding the surgical arm 120 (for example, the numbers of joints and links constituting the surgical arm 120, the status of connection between the joints and the links, and the length of the links).

The whole body cooperative control unit 930 is a functional block that, on the basis of the motion purposes and constraint conditions of the surgical arm 120, calculates the torque command value $\tau_a$ to the joint unit 912 in the operation space by computation using the generalized inverse dynamics. The whole body cooperative control unit 930 includes a joint state acquisition unit 931, the computational condition setting unit 932, a virtual force estimation unit 933, and a real force calculation unit 934.

The state acquisition unit 931 can acquire the rotation angle of the joint unit 912 detected by the joint state detection unit 912-1 and an external torque acting on the joint 912. Furthermore, the storage unit 960 stores various kinds of information to be processed by the control system 900. Specifically, the storage unit 960 stores various kinds of arm information regarding the surgical arm 120 (for example, the numbers of the joints and the links constituting the surgical arm 120, the status of connection between the links and the joints, and the length of the links) (as described above). The state acquisition unit 931 can acquire such arm information from the storage unit 960. Therefore, on the basis of the state of the joint unit 912 and the arm information, the state acquisition unit 931 can acquire information regarding the plurality of joints, the plurality of links, and the position of the imaging unit in the space (coordinates) (in other words, the shape of the surgical arm 120, and the position and posture of the imaging unit), and forces acting on the joints, the links, and the imaging unit, as an arm state. The state acquisition unit 931 transmits the acquired arm information to the computational condition setting unit 932. Furthermore, the state acquisition unit 931 can also acquire the inclination angle of the surgical arm device 100 or the surgical arm 120 detected by the inclination detection unit 911.

The computational condition setting unit 932 sets computational conditions for computations in relation to the whole body cooperative control using generalized inverse dynamics. The computational conditions here are motion purposes and constraint conditions, for example. The motion purposes are various kinds of information regarding the motion of the surgical arm 120, specifically, the target values of the position and posture (coordinates), speed, acceleration, force, and the like of the imaging unit, and the target values of the positions (coordinates), speeds, accelerations, forces, and the like of the plurality of joint units and the plurality of links constituting the surgical arm 120. Furthermore, the constraint conditions here are various kinds of information for limiting or constraining the motion of the surgical arm 120, specifically, the values of the coordinates of a region where the constituent members of the surgical arm 120 are unmovable, the speeds at which the constituent members of the surgical arm 120 are unmovable, the accelerations of the constituent members of the surgical arm 120, the forces the constituent members of the surgical arm 120 are incapable of generating, and the like.

Furthermore, the computational condition setting unit 932 sets the gravity force, Coriolis' force, and centrifugal force b depending on the inclination angle of the surgical arm device 100 or the surgical arm 120 acquired by the state acquisition unit 931 according to the foregoing equation (6).

Furthermore, the computational condition setting unit 932 may set the limit ranges of various physical amounts that the surgical arm 120 cannot structurally implement, as constraint conditions. Furthermore, the computational condition setting unit 932 may have a physical model of structure of the surgical arm 120 (for example, a model of the number and length of the links constituting the surgical arm 120, the status of connection between the links via the joint units, and the movable ranges of the joint units), and may set motion conditions and constraint conditions by generating a control model reflecting desired motion conditions and constraint conditions on the physical model.

In the present embodiment, appropriately setting the motion purposes and the constraint conditions allows the surgical arm 120 to perform the desired actions. For example, it is a matter of course that setting the target value of the position of the imaging unit as the end effector 110 as a motion purpose allows the imaging unit to move to the target position. Furthermore, setting a constraint condition such that the surgery arm 120 does not enter a predetermined region in the space (for example, such that the surgical arm 120 does not invade the body cavity of the patient) allows the surgical arm 120 to be driven under the constraint of movement.

A specific example of motion purpose is a pivot action by which, while the imaging direction of the imaging unit as the end effector 110 is fixed to a direction to a specific portion to be operated, the imaging unit pivots in a plane of a circular cone with the tip at the specific portion to be operated around the axis of the circular cone as a pivotal axis. In the pivot action, for example, the imaging unit pivots while the distance between the imaging unit and a point corresponding to the tip of the circular cone is kept constant. The pivot action of such an imaging unit makes it possible to observe the observation portion from different angles at an equal distance to improve the convenience of the operator.

Furthermore, another specific example of motion purpose may be a control of torque generated at the joint units constituting the surgical arm 120. Specifically, the motion purpose may be a power-assist action of controlling the state of joint units 130 to cancel out the gravity force acting on the arm unit 120 and controlling the states of the joint units to support the movement of the arm unit 120 to the direction of an externally applied force. In the power-assist action, the driving of the joint units is controlled to generate torque canceling out external torque due to the gravity force at the joint units constituting the surgical arm 120, so that the position and posture of the surgical arm 120 can be held in a predetermined state. In a case where external torque is further applied from the outside (for example, from the user), the driving of the joint units is controlled to generate generative torque in the same direction as the applied external torque. In a case where the user manually moves the surgical arm 120, performing such power-assist action allows the user to manually move the surgical arm 120 by a smaller force and feel as if he/she moves the surgical arm 120 in zero gravity. Furthermore, the pivot action and the power-assist action may be combined together.

In the present embodiment, the motion purpose is a concept including both an instantaneous motion purpose (for example, the target values of the position, speed, force, and the like of the constituent members of the surgical arm 120 at a certain time) and motion of the constituent members of the surgical arm 120 implemented with time as a result of continuous attainment of the instantaneous motion purpose. For example, in the pivot action described above, although the pivot action of the imaging unit is a motion purpose unto itself, the values of the position and speed of the imaging unit in the plane of the circular cone during the pivot action are set as instantaneous motion purposes (the target values for the motion purposes). Furthermore, in the power-assist action, although performing the power-assist action to support the movement of the surgical arm 120 to the direction of the externally applied force is the motion purpose unto itself, the value of the generative torque to the same direction as the external torque applied to the joint units during the power assist action is set as an instantaneous motion purpose (the target value for the motion purpose). In each of steps of computations for the whole body cooperative control by a whole body coordination controller 240, the instantaneous motion purposes are set every time and the computations are repeatedly performed to finally attain the desired motion purpose.

Note that, at the time of setting the motion purposes by the computational condition setting unit 932, the viscosity resistance coefficient in the rotational motion of each of the joint units may also be set as appropriate (as far as the actuator for joint drive is configured to adjust the viscosity resistance coefficient in the rotational motion). For example, according to the motion purpose to be set, the joint units can be set to the state easy to rotate or the state hard to rotate with respect to the externally applied force. Specifically, in the power-assist action, setting a small viscosity resistance coefficient to the joint units allows the user to move the surgical arm 120 by a smaller force and feel a sensation of weightlessness.

Furthermore, the computational condition setting unit 932 may set the motion purpose on the basis of the state of the surgical arm 120 acquired by the state acquisition unit 931. For example, in a case where the user wishes to move manually the surgical arm 120, the state acquisition unit 931 acquires the position information of the surgical arm 120 and the information regarding the force acting on the surgical arm 120, and the computational condition setting unit 932 can set the position, speed, force, and the like of movement of the surgical arm 120 by the user as an instantaneous motion purpose. According to the method for setting such a motion purpose, it is possible to control the driving of the surgical arm 120 to follow and support the movement of the surgical arm 120 by the user.

Furthermore, the computational condition setting unit 932 may set the motion purposes and the constraint conditions according to the instruction from the user via the input unit 950. For example, according to the operation performed by the user on the operation device such as the lever or the pedal provided as the input unit 950, the computational condition setting unit 932 may set the instantaneous motion purposes such as the positions and speeds of the constituent members of the surgical arm 120.

Furthermore, in a case where the computational conditions such as the motion purposes and the constraint conditions are stored in the storage unit 960, the computational condition setting unit 932 can set the computational condition read from the storage unit 960. For example, in a case where the motion purpose is to cause the imaging unit as the end effector 110 to stand still at a predetermined position in the space, the coordinates of the predetermined position can be pre-stored in the storage unit 960 as the motion purpose. Furthermore, for example, in a case where the motion purpose is to cause the imaging unit to move in a predetermined path in the space, the coordinates of a plurality of points that can interpolate the path can be pre-stored in the storage unit 960 as the motion purpose. Furthermore, in a case where the motion purpose is the pivot action of the imaging unit (as described above), the target values of the position, speed, and the like of the imaging unit pivoting in the plane of the circular cone can be pre-stored in the storage unit 960. Furthermore, in a case where the motion purpose is the power-assist action, the target value of the force can be pre-stored in the storage unit 960. Note that the priorities of the motion purposes can be set to the constraint conditions stored in the storage unit 960. In a case where there is a plurality of different motion purposes, the computational condition setting unit 932 may set the motion purpose according to the priority of the constraint condition.

So far, examples of methods for setting by the computational condition setting unit 932 computational conditions to be used in generalized inverse dynamics computation such as motion purposes and constraint conditions have been described. Which of these methods to be used may be selected as appropriate by the user according to the use purpose of the surgical arm device 100 or the like. As a matter of course, the plurality of methods exemplified above may be combined to set the computational conditions by the computational condition setting unit 932. The computational condition setting unit 932 transmits to the virtual force estimation unit 933 the state of the surgical arm device 100 received from the state acquisition unit 931 and the motion conditions and constraint conditions set by the computational condition setting unit 932 itself.

The virtual force estimation unit 933 performs a computation using the generalized inverse dynamics according to the virtual force calculation process to calculate the virtual force $f_v$ relating to the whole body cooperative control. The virtual force estimation unit 993 transmits the calculated virtual force $f_v$ to the real force calculation unit 934.

The real force calculation unit 934 solves the condition for implementing the generalized force $\tau_v$ ($=J_v^T f_v$) by a virtual force from the generative torque $\tau_a$ generated at the joint units and the external force $f_e$ as a secondary planning problem according to the real force calculation process described above to calculate the real force $\tau_a$. The real force calculation unit 934 transmits the calculated real force $\tau_a$ as a torque command value to the ideal joint control unit 940.

The bias acceleration c of the operation space (for example, the joint space of the multi-link structural body) expressed in the foregoing equation (5) includes the b term corresponding to gravity force, Coriolis' force, and centrifugal force. In a case where the surgical arm device 100 is attached to a movable operating table, the Z-axis direction in the local coordinate system changes along with the inclination of the operating table 300 (or the patient support surface), so that the gravity force acting on the surgical arm 120 may not always coincide with the Z direction in the local coordinate system. As described above, in the present embodiment, the gravity force g, Coriolis' force, and the centrifugal force v are treated as a function of the joint angle or joint angular velocity (corresponding to the inclination angle of the surgical arm device 100 detected by the inclination detection unit 911) as expressed in the foregoing equation (6). Accordingly, the virtual force estimation unit 933 can estimate the virtual force to which gravity compensation is made to the correct direction of the gravity force by a computation based on the generalized inverse dynamics using the motion equation including the operation space bias acceleration c with the term of the gravity force acting to the correct direction of the gravity force according to the present inclination angle of the surgical arm device 100 main body acquired by the inclination detection unit 911. Accordingly, the real force calculation unit 934 can calculate the real force to which gravity compensation is made in the correct direction of the gravity force and pass the same to the ideal joint control unit 940.

The ideal joint control unit 940 is a functional module that, in the force control on the joint unit 912, corrects responses of an actuator driving the joint unit 912 according to a logical model while avoiding influence of disturbances resulting from parameters of dynamics difficult to model and identify such as the friction and inertia of the actuator. The ideal joint control unit 940 includes a disturbance estimation unit 941 and a command value calculation unit 942.

The disturbance estimation unit 941 estimates the torque acting on the joint torque on the basis of the rotation angular velocity calculated from the rotation angle q detected by the joint state detection unit 912-2 (the encoder 703 attached to the output shaft of the decelerator 702 in the actuator 700), and estimates the disturbance torque $\tau_d$ from the difference between the estimated torque and the torque command value $\tau$.

The command value calculation unit 942 uses the disturbance torque $\tau_d$ estimated by the disturbance estimation unit 941 to calculate the torque command value $\tau$ to be generated at the joint unit 912. Specifically, the command value calculation unit 942 adds the disturbance torque $\tau_d$ to the torque target value $\tau^{ref}$ calculated from the ideal response model of the joint unit 912 expressed in the foregoing equation (15) to calculate the torque command value $\tau$. Then, the command value calculation unit 942 transmits the calculated torque command value $\tau$ to the drive control unit 913. The drive control unit 913 controls the rotation angle and the generative torque of the joint units 912 according to the torque command value $\tau$.

As described above, the control system 900 executes the whole body cooperative control of the surgical arm 120 and various computations relating to the ideal joint control of the joint units 912 on the basis of the joint state of the surgical arm device 100, the motion purposes, and the constraint conditions, and transmits the torque command value x obtained as computation results to the surgical arm device 100. On the other hand, the surgical arm device 100 controls the driving of the joint units 912 constituting the surgical arm 120 according to the received torque command value $\tau$ and detects the joint state of the joint units 912 during and after driving, and transmits the detection results to the control system 900. During driving of the surgical arm device 100, such transmissions and receptions between the control system 900 and the surgical arm device 100 are continuously repeated.

INDUSTRIAL APPLICABILITY

The technique disclosed herein has been described in detail so far with reference to specific embodiments. However, it is obvious that persons skilled in the art can achieve modifications and replacements of the embodiments without deviating from the gist of the technique disclosed herein.

In the embodiments described herein, the technique disclosed herein is mainly applied to a surgical arm device. However, the gist of the technique disclosed herein is not limited to these embodiments but is also applicable in a similar manner to force-controlled arm devices used for medical purposes other than surgery or various technical fields other than the medical field.

Briefly, the technique disclosed herein has been described in the form of exemplification, and thus the description herein should not be interpreted in a limited way. The gist of the technique disclosed herein should be interpreted with reference to the claims.

Note that the technique disclosed herein can also be configured as follows:

(1) A control system that controls a surgical arm device, including:

an inclination information acquisition unit that acquires inclination information of the surgical arm device;

a setting unit that sets a computational condition including gravity compensation according to the inclination information; and a computation unit that calculates a command value to the surgical arm device according to the computational condition.

(2) The control system according to (1), in which the inclination information acquisition unit acquires inclination information resulting from inclination of an operating table to which the surgical arm device is attached.

(3) The control system according to (2), in which the inclination information is angle information.

(4) The control system according to (2), in which the inclination information acquisition unit acquires information regarding an inclination angle of a patient support surface of the operating table.

(5) The control system according to any of (1) to (4), in which the surgical arm device includes a multi-link structural body in which a plurality of links is coupled together by a joint unit, the computational condition setting unit sets a motion purpose and a constraint condition of the multi-link structural body in an operation space describing inertia of force acting on the multi-link structural body and acceleration of the multi-link structural body in generalized inverse dynamics, and the computation unit calculates a virtual force that acts on the operation space to implement the operation space acceleration indicating the motion purpose, on the basis of a motion equation relating to the operation space including a term of an operation space bias acceleration in consideration to the gravity compensation according to the inclination information, converts the virtual force to a real force in consideration to the constraint condition, and calculates a torque command value for driving the joint unit on the basis of the real force.

(6) The control system according to (4), in which the computation unit makes a further correction to the real force such that the joint unit does not deviate from a logical response model.

(7) The control system according to (6),
in which the computation unit corrects a torque target value calculated on the basis of the logical response model according to the real force and external torque acting on the joint unit by using disturbance torque of the joint unit to calculate the torque command value.

(8) The control system according to (7),
in which the computation unit estimates torque acting on the joint unit from an angular velocity of the joint unit, and estimates the disturbance torque on the basis of a difference between the estimated torque and the torque command value.

(9) A control method for controlling a surgical arm device, including:
an inclination information acquisition step of acquiring inclination information of the surgical arm device;
a setting step of setting a computational condition including gravity compensation according to the inclination information; and
a computation step of calculating a command value to the surgical arm device according to the computational condition.

(10) A surgical arm system including:
a multi-link structural body in which a plurality of links is coupled by a joint unit;
an inclination information acquisition unit that acquires inclination information of the multi-link structural body;
a joint state detection unit that detects a state of the joint unit; and
a drive control unit that controls driving of the joint unit according to a command value calculated depending on the inclination information and the state of the joint unit.

(11) The surgical arm system according to (10),
in which the inclination information acquisition unit acquires inclination information resulting from inclination of an operating table to which the surgical arm device is attached.

(12) The surgical arm system according to (11),
in which the inclination information is angle information.

(13) The surgical arm system according to (11),
in which the inclination information acquisition unit acquires information regarding an inclination angle of a patient support surface of the operating table.

(14) The surgical arm system according to any one of (10) to (13),
in which, in generalized inverse dynamics, for implementing an operation space acceleration indicating a motion purpose of the multi-link structural body in an operation space describing an inertia of force acting on the multi-link structural body and an acceleration of the multi-link structural body, the drive control unit drives the joint unit according to a torque command value that is based on a real force obtained by converting a virtual force acting on the operation space calculated on the basis of a motion equation relating to the operation space including a term of an operation space bias acceleration in consideration to gravity compensation according to the inclination information.

(15) The surgical arm system according to (14),
in which the drive control unit drives the joint unit according to a torque command value based on the real force to which a correction is made such that the joint unit does not deviate from a logical response model.

(16) The surgical arm system according to (15),
in which the joint unit is driven according to a torque command value in which a torque target value calculated on the basis of the logical response model according to the real force and external torque acting on the joint unit is corrected using disturbance torque based on a difference between estimated torque acting on the joint unit and a torque command value.

REFERENCE SIGNS LIST

100 Surgical arm device
110 End effector
111 Wrist joint
120 Surgical arm
200 Carriage
300 Operating table
600 Control system
601 State acquisition unit
602 Computational condition setting unit
603 Force computation unit
604 Command value conversion unit
611 Inclination detection unit
612 Joint unit
612-1 Joint state detection unit
612-2 Joint drive unit
613 Drive control unit
700 Actuator
701 Motor
702 Decelerator
703 Encoder
704 Torque sensor
801 Computing unit (ideal response model)
802 Computing unit (torque calculation)
803 Joint (transfer function $1/J_n$)
804 Computing unit (differentiation operation)
810 Disturbance observer
811 Computing unit (acting torque estimation)
812 Computing unit (low pass filter)
900 Control system
911 Inclination detection unit
912 Joint unit
912-1 Joint state detection unit
912-2 Joint drive unit
913 Drive control unit
920 Display device
930 Whole body cooperative control unit
931 State acquisition unit
932 Computational condition setting unit
933 Virtual force estimation unit
934 Real force calculation unit
940 Ideal joint control unit
941 Disturbance estimation unit
942 Command value calculation unit
950 Input unit
960 Storage unit

The invention claimed is:
1. A control system that controls a surgical arm device, comprising:
processing circuitry configured to
acquire inclination information of the surgical arm device, the inclination information resulting from inclination of an operating table to which the surgical arm device is attached;
calculate a correct direction of gravity force based on the inclination information;
set a computational condition including gravity compensation that compensates for the gravity force in the calculated correct direction of the gravity force; and
calculate a command value to the surgical arm device according to the computational condition.

2. The control system according to claim 1,
wherein the inclination information is angle information.

3. The control system according to claim 1,
wherein the processing circuitry acquires information regarding an inclination angle of a patient support surface of the operating table.

4. The control system according to claim 1, wherein
the surgical arm device includes a multi-link structural body in which a plurality of links is coupled together by a joint,
the processing circuitry sets a motion purpose and a constraint condition of the multi-link structural body in an operation space describing inertia of force acting on the multi-link structural body and acceleration of the multi-link structural body in generalized inverse dynamics, and
the processing circuitry calculates a virtual force that acts on the operation space to implement the operation space acceleration indicating the motion purpose, on a basis of a motion equation relating to the operation space including a term of an operation space bias acceleration in consideration to the gravity compensation according to the inclination information, converts the virtual force to a real force in consideration to the constraint condition, and calculates a torque command value for driving the joint on a basis of the real force.

5. The control system according to claim 4,
wherein the processing circuitry makes a further correction to the real force such that the joint does not deviate from a logical response model.

6. The control system according to claim 5,
wherein the processing circuitry corrects a torque target value calculated on a basis of the logical response model according to the real force and external torque acting on the joint by using disturbance torque of the joint to calculate the torque command value.

7. The control system according to claim 6,
wherein the processing circuitry estimates torque acting on the joint from an angular velocity of the joint, and estimates the disturbance torque on a basis of a difference between the estimated torque and the torque command value.

8. A control method for controlling a surgical arm device, comprising:
acquiring, using processing circuitry, inclination information of the surgical arm device, the inclination information resulting from inclination of an operating table to which the surgical arm device is attached;
calculating, using the processing circuitry, a correct direction of gravity force based on the inclination information;
setting, using the processing circuitry, a computational condition including gravity compensation that compensates for the gravity force in the calculated correct direction of the gravity force;
calculating, using the processing circuitry, a command value to the surgical arm device according to the computational condition; and
issuing, using the processing circuitry, the command value to the surgical arm device.

9. A surgical arm system comprising:
a multi-link structural body in which a plurality of links is coupled by a joint; and
processing circuitry configured to
acquire inclination information of the multi-link structural body, the inclination information resulting from inclination of an operating table to which the multi-link structural body is attached,
calculate a correct direction of gravity force based on the inclination information,
set a computational condition including gravity compensation that compensates for the gravity force in the calculated correct direction of the gravity force,
acquire a state of the joint,
calculate a command value to the multi-link structural body according to the computational condition and the state of the joint, and
control driving of the joint according to the calculated command value.

10. The surgical arm system according to claim 9,
wherein the inclination information is angle information.

11. The surgical arm system according to claim 9,
wherein the processing circuitry acquires information regarding an inclination angle of a patient support surface of the operating table.

12. The surgical arm system according to claim 9,
wherein, in generalized inverse dynamics, for implementing an operation space acceleration indicating a motion purpose of the multi-link structural body in an operation space describing an inertia of force acting on the multi-link structural body and an acceleration of the multi-link structural body, the processing circuitry drives the joint according to a torque command value that is based on a real force obtained by converting a virtual force acting on the operation space calculated on a basis of a motion equation relating to the operation space including a term of an operation space bias acceleration in consideration to gravity compensation according to the inclination information.

13. The surgical arm system according to claim 12,
wherein the processing circuitry drives the joint according to a torque command value based on the real force to which a correction is made such that the joint does not deviate from a logical response model.

14. The surgical arm system according to claim 13,
wherein the joint is driven according to a torque command value in which a torque target value calculated on a basis of the logical response model according to the real force and external torque acting on the joint is corrected using disturbance torque based on a difference between estimated torque acting on the joint and a torque command value.

* * * * *